United States Patent [19]

Bozzelli et al.

[11] Patent Number: 4,582,805

[45] Date of Patent: Apr. 15, 1986

[54] IMMOBILIZATION OF BIOLOGICAL MATTER VIA COPOLYMERS OF ISOCYANATOALKYL ESTERS

[75] Inventors: John W. Bozzelli; Roberta C. Cheng, both of Midland, Mich.

[73] Assignee: The Dow Chemical Company, Midland, Mich.

[21] Appl. No.: 567,125

[22] Filed: Dec. 29, 1983

Related U.S. Application Data

[63] Continuation-in-part of Ser. No. 374,224, May 3, 1982, abandoned.

[51] Int. Cl.$^4$ .................... C12N 11/08; C12N 11/02; C12N 11/06
[52] U.S. Cl. .................................. 435/180; 435/177; 435/181
[58] Field of Search ............... 435/174, 177, 180, 181, 435/182

[56] References Cited

U.S. PATENT DOCUMENTS

| | | | |
|---|---|---|---|
| 3,672,955 | 6/1972 | Stanley | 195/68 |
| 3,767,790 | 10/1973 | Guttag | 424/81 |
| 4,177,038 | 12/1979 | Biebricher et al. | 8/192 |
| 4,195,129 | 3/1980 | Fukui et al. | 435/182 |
| 4,308,349 | 12/1981 | Foley et al. | 435/253 X |
| 4,312,946 | 1/1982 | Wood et al. | 435/182 |
| 4,440,903 | 4/1984 | Golstein et al. | 435/181 X |
| 4,504,628 | 3/1985 | Johnson | 525/278 |

FOREIGN PATENT DOCUMENTS

874457 6/1971 Canada ..................... 260/454.5

OTHER PUBLICATIONS

Fusee et al., "Immobilization of *Escherichia coli* Cells Containing Aspartase Activity with Polyurethane and its Application for L-Aspartic Acid Production", *Applied and Environmental Microbiology*, Oct. 1981, pp. 672-676.

Sonomoto et al., "Application of Urethane Prepolymers to Immobilization of Biocatalysts: Δ-Dehydrogenation of Hydrocortisone by Arthrobacter Simplex Cells Entrapped with Urethane Prepolymers", *Agri. Biol. Chem.* 44(5), 1119-1126, (1980).

Goldstein, "Chemically Modified Polymers Containing Isocyanide Functional Groups as Supports for Enzyme Immobilization", *Biotech. Applns of Proteins and Enzymes*, Acad. Press NY, 1977, pp. 153-167.

*Primary Examiner*—David M. Naff
*Attorney, Agent, or Firm*—Donald L Corneglio, Jr.

[57] ABSTRACT

A process is disclosed for the chemical immobilization of biological material such as bacteria and enzymes containing an active hydrogen with a vinyl addition polymer of an isocyanatoalkyl ester of an ethylenically unsaturated carboxylic acid. The vinyl addition polymer is versatile in that it can be copolymerized with varying amounts and types of comonomers.

16 Claims, No Drawings

IMMOBILIZATION OF BIOLOGICAL MATTER VIA COPOLYMERS OF ISOCYANATOALKYL ESTERS

RELATED U.S. APPLICATION DATA

This Application is a continuation-in-part of Application Ser. No. 374,224, filed May 3, 1982, now abandoned.

BACKGROUND OF THE INVENTION

The present invention generally relates to the chemical immobilization of biological materials. Further, the present invention is directed toward immobilization carried out with a vinyl addition polymer containing a pendent isocyanate group which forms a urethane type linkage with the biological material.

The immobilization of biological materials is the process of localizing biological molecules for use in a wide variety of experimental and commercial processes. Biological material may be a substance which is capable of interacting with other biological material. For example, it may be proteins, enzymes, plant and animal cells, fungal cells, algal cells, bacterial cells or organic matter with biological activity.

Processes for immobilizing biological material generally falls into two classes, physical and chemical. Physical methods consist simply of restricting the movement of the biological material to a microspace created by a compound structure, by a gel or other similar means. Chemical techniques can be more complicated as the process must immobilize the biological material by a chemical interaction, such as covalent bonds, without altering the reactivity of the biological material.

Some attempts to isolate biological material employ a polyurethane polymer for inclusion of enzymes in microbial cells inside the polymer matrixes. Still other processes use a urethane prepolymer whereby gels of a particular physical and chemical property are obtained for the inclusion of biological material. Both of these processes are considered physical methods of immobilization. See in general: Fusee et al., "Immobilization of *Escherichia Coli*", *Applied and Environmental Microbiology*, 42 (4), p. 672–76, October, 1981; and Sonomoto et al., "Application of Urethane Prepolymer to Immobilization of Biocatalysts", *Agric. Biol. Chem.*, 44 (5), p. 1119–26, 1980.

Other attempts to immobilize biological material employ chemical means which are capable of forming chemical bonds to the biologically active matter. U.S. Pat. No. 4,177,038 utilizes a bonding agent between a vehicle substance and the biological material. The coupling agent between the vehicle and the biological material can be an isocyanate group. The vehicle is synthesized to contain a reactive isocyanate to which the biological material can be covalently bonded. Still, another attempt to chemically bond biological material is provided by U.S. Pat. No. 4,312,946 wherein an isocyanate-capped polyurethane foam is employed to covalently bond with one or more amine groups on an enzyme. This process is closely related to U.S. Pat. No. 3,672,955 which employs a similar means but not as a polyurethane foam.

Unfortunately, the physical or chemical methods of immobilizing biological material has a tendency to reduce the activity of the biological material. This is especially true of enzymes. Also, upon immobilization, enzymes can have reduced thermal, storage, pH, proteolytic or organic solvent stability. It, therefore, would be desirable to have a process for immobilizing biological material whereby a significant portion of its original activity was maintained. It would be even more desirable to be able to chemically immobilize the biological material such that the particular immobilizing agent could be modified and adjusted to the various conditions in which the biological material was to be employed. This would in turn maximize the effectiveness of the immobilized biological material and its range of application.

SUMMARY OF THE INVENTION

In one aspect, the present invention is a process for chemically immobilizing biological material containing an active hydrogen moiety comprising the steps of contacting the biological material with a vinyl addition polymer comprising a biological immobilizing amount of a polymerized isocyanatoalkyl ester of ethylenically unsaturated carboxylic acid and reacting the isocyanate moiety pendent from the backbone of the vinyl addition polymer with the active hydrogen moieties of the biological material to form a urethane type linkage. The vinyl addition polymer can be a copolymer containing a monomer such that said copolymer is more hydrophilic than a 40/60 weight percent copolymer of an isocyanate monomer in methyl methacrylate. The biological material can be an enzyme or a bacterial cell. Preferably, the bacterial cell is chosen from the Ampullariella species 3876, 3877, 3965 or 3966. The preferred isocyanatoalkyl ester is 2-isocyanatoethyl methacrylate. The vinyl addition copolymer is preferably a copolymer comprising 2-isocyanatoethyl methacrylate and N,N'-dimethylacrylamide.

The present invention further provides for the product formed from the process for immobilizing biological material as described above. Still further, the present invention provides a means for adjusting the immobilizing biological material whereby the product can be adjusted to changing environments. This is made possible by the utilization of a vinyl addition polymer comprising a biologically immobilizing amount of a polymerized isocyanatoalkyl ester of an ethylenically unsaturated carboxylic acid such that the cyanate group is pendent from the backbone of the vinyl addition polymer.

DETAILED DESCRIPTION OF THE INVENTION

The process of the invention requires a polymer containing an isocyanatoalkyl ester of an ethylenically unsaturated carboxylic acid. Desirably, these esters correspond to the formula:

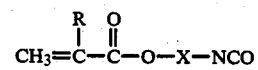

in which R is H—, CH$_3$— or CH$_3$—CH$_2$—; and X is a C$_1$ to C$_{12}$ alkyl group. More preferred are those esters wherein R is H— or CH$_3$—; and X is a C$_1$ to C$_5$ alkyl group. Most preferred are 2-isocyanatoethyl methacrylate and 2-isocyanatoethyl acrylate. The preparation of these materials is taught, for instance, in Canadian Patent No. 874,457.

While the isocyanatoalkyl esters used in the invention may be homopolymerized, desirably, they are copolymerized with other addition polymerization monomers to form a vinyl addition polymer. The selection of the particular comonomer or comonomers to be employed is not critical to the practice of the invention, however, as discussed hereinafter, in some use environments, proper selection of comonomers can greatly enhance the performance of the chemically immobilized matter.

If the immobilized biological matter is to be used in an aqueous environment, it is desirable that the comonomers employed in the polymerization render the copolymer at least as hydrophilic as a 40/60 (weight percent) copolymer of the isocyanate monomer and methyl methacrylate would be. It is more desirable that the copolymer be rendered at least as hydrophilic as an 80/20 (weight percent) copolymer of the isocyanate monomer and N,N'-dimethylacrylamide would be. A further limitation on the choice of comonomers is that a comonomer generally should not contain excessive amounts of moieties which are substantially reactive with isocyanate moieties under addition polymerization conditions. Generally, suitable comonomers include monovinylidene aromatic monomers such as styrene and β-methyl styrene; ethylenically unsaturated carboxylic acids such as acrylic acid and methacrylic acid; esters of ethylenically unsaturated carboxylic acids such as methyl methacrylate and butyl acrylate; esters of ethylenically unsaturated alcohols such as vinyl acetate (these may be hydrolyzed to yield polyalcohols); vinyl pyridines and salts thereof; vinyl pyrrolidones such as N-vinyl pyrrolidone; and amides such as acrylamide and N,N'-dimethylacrylamide. Because of its wide availability and excellent performance, N,N'-dimethylacrylamide is especially preferred as a comonomer.

The monomers are polymerized using conventional addition polymerization techniques well known to those in the art. The polymerization may take place in bulk or in solution. If the polymerization takes place in solution, it is desirable to remove the solvent before contacting the polymer with the enzyme. As stated above, it is generally desirable that the polymer be relatively hydrophilic. However, the hydrophilicity and the molar mass of the polymer must be such that the polymer is not water-soluble if the immobilized enzyme is to be used in an aqueous environment.

By "not water-soluble" is meant that after the immobilization has taken place, the polymer system should remain a sufficiently coherent mass so that it is retrievable from a liquid system. Thus, a polymer may be very hydrophilic, provided that the molar mass is sufficiently high, or may have a very low molar mass, provided that the solubility is sufficiently low. The molar mass (molecular weight) of the polymer may vary over a wide range, depending upon the solubility of the polymer, but the number average molar mass is desirably between 6,000 and 50,000. If the isocyanate polymer is copolymerized from non-isocyanate monomers, the polymer chains generally have an average desirably of at least two, more desirably of at least three, and preferably of more than four isocyanate moieties per polymer molecule. The copolymers also generally contain desirably at least 5, more desirably at least 10, and preferably at least 30, weight percent of isocyanate monomer.

The practice of the invention contemplates the chemical immobilization of biological material containing an active hydrogen moiety. Biological material is meant to include any organic compound or organic structure metabolically produced by a living organism, or any synthetic duplication or variation thereof. Generally the immobilization of the biological material entails the formation of a urethane type linkage between the active isocyanate group, pendent from the vinyl addition polymer, and the biological material which contains an active hydrogen moiety. The isocyanate containing comonomer is provided by the isocyanatoalkyl ester which is addition copolymerized with selected comonomers to form a vinyl addition polymer.

The biological material to be chemically immobilized contains an active hydrogen moiety. An active hydrogen moiety is meant to include any hydrogen which displays significant activity, according to the Zerewitnoff test described by Woller in *Journal of American Chemical Society*, Vol. 49, p. 3181 (1927). Specifically included within the definition of active hydrogen are alcohols, primary and secondary amines, amides, mercaptans and acids.

Examples of compounds which are important biological materials include amino acids, proteins, DNA, RNA, enzymes, carbohydrates, etc. Examples of structures which are important biological materials include bacterial, fungal, algal, animal and plant cell walls, mitochondria, nucleus walls, and plant and animal tissues.

Although generally any biological material is suitable for use in the invention, in a preferred embodiment, they are limited to enzymes and bacterial cells. In the case of bacterial cells, they are generally immobilized to take advantage of the intracellular enzymes they contain. Although the invention may be carried out using any cell or enzyme which is reactive with the pendent isocyanate groups, in a more preferred embodiment bacteria of the genus Ampullariella are contacted with a hereinbefore described polymer to provide a source of immobilized glucose isomerase. Preferred species of Ampullariella include 3876, 3877, 3965 and 3966. Especially preferred is species 3876. A full disclosure of these species is contained in U.S. Pat. No. 4,308,349, which is incorporated herein by reference.

The enzyme, cell or other biological material is conveniently mixed with the vinyl addition polymer and subjected to mild agitation or stirring. The mixing need take place only over a relatively short period of time, for instance, from 0.25 to 480 minutes. Generally, a urethane catalyst such as dibutyltin dilaurate can be used to promote the reaction of the isocyanate groups and the active hydrogen moieties in the biological material. The immobilization generally takes place at room temperature (elevated temperatures may degrade enzymes) or in an aqueous environment. Although water will compete with the biological material for reaction with isocyanate groups; however, if the cell or enzyme is sufficiently reactive and the number of isocyanate moieties is sufficiently high, the competing water reaction may not have a significant effect on the final product. The number of isocyanate moieties present in the vinyl addition polymer is variable depending on the amount of isocyanatoalkyl ester comonomer employed in the copolymerization. Therefore, one can vary the amount of isocyanate groups which are pendent from the polymer to provide the desired biological immobilizing amount of the polymerized isocyanatoalkyl ester.

After the biological material has been reacted with the polymer, it is ready for use. However, especially in the case of cells and enzymes, it is generally more convenient to further process the immobilized product, as by pelletizing. If more convenient, the enzyme may be pelletized during or even before the immobilization reaction. Typically, the immobilized enzyme may be pressed into tablets or pellets for ease of handling and to prevent dispersion of the material under catalytic conditions. Typically, tablets of the immobilized enzyme will be placed into a column and the materials to be reacted will be passed through the column where it contacts the immobilized enzyme.

The invention will be further illustrated by the following examples. Unless otherwise specified, all parts are by weight.

EXAMPLE 1

A. Preparation of Polymer

A three-necked flask, equipped with a stirrer, a reflux condenser and addition funnel was purged with $N_2$ and charged with 50 parts of 2-ethoxyethyl acetate solvent. A mixture of 1.0 part azobisisobutyronitrile (AIBN) (initiator) and 50 parts of monomer mixture (35/35/30 methyl methacrylate/ethyl acrylate/2-isocyanatoethyl methacrylate) was added to the addition funnel. The flask was heated to 100° C. and the monomer/initiator mixture added dropwise over a period of 3 hours.

B. Immobilization

In a series of trials, 2.0 g of Ampullariella species 3876 was added to a flask, followed by varying amounts of the polymer of Part A, followed by varying amounts of water, and finally followed by 1.0 g of a 10-percent solution of dibutyltin dilaurate (catalyst) in 2-ethoxyethyl acetate. The mixture was cured in a vacuum oven for varying periods of time at 60° C.

C. Enzyme Activity

Glucose isomerase activity was measured by incubation of the immobilized enzyme sample (about 10 mg) in 5 ml of a substrate solution (made up from 50 g anhydrous D-glucose, 238 mg cobalt chloride·6 $H_2O$, 14.5 g maleic acid, 9.5 g sodium hydroxide, 12.4 g magnesium sulfate·7 $H_2O$, and 5 g potassium chloride, combined and diluted to 1 liter with distilled, deionized $H_2O$, and adjusted to pH 6.5) at 70° C. for 30 minutes. The fructose formed was measured spectrophotometrically by the cystein-carbozoyl method taught in J. Biochem. 192, 583 (1951). The results are shown in Table I.

TABLE I

| Sample | Polymer (g) | $H_2O$ (g) | Cure (min) | Activity (% of Original) |
| --- | --- | --- | --- | --- |
| 1-1 | 2.0 | — | 30 | 16.3 ± 0.54 |
| 1-2 | 1.0 | — | 30 | 24.0 ± 1.66 |
| 1-3 | 2.0 | 0.03 | 30 | 18.9 ± 0.80 |
| 1-4 | 2.0 | — | 60 | 12.9 ± 1.61 |
| 1-5 | 1.0 | — | 60 | 16.0 ± 3.44 |
| 1-6 | 2.0 | 0.04 | 60 | 15.2 ± 1.07 |

EXAMPLE 2

Using the materials of Example 1, varying proportions of polymer, catalyst solution and water were combined with 1.0 g of bacterium and cured for various periods of time at various temperatures. These results are shown in Table II.

TABLE II

| Sample | Polymer (g) | Catalyst (g) | $H_2O$ (g) | 60° C. Cure (min) | Activity (% of Original) |
| --- | --- | --- | --- | --- | --- |
| 2-1 | 0.5 | 1.0 | — | 30 | 23.2% 1.2 |
| 2-2 | 0.5 | 1.0 | — | 15 | 31.9% 4.2 |
| 2-3 | 0.5 | 1.0 | — | 7.5 | 22.5% 2.5 |
| 2-4 | 0.5 | 1.0 | 0.1 | 30 | 20.3% 1.0 |
| 2-5 | 0.5 | 1.0 | 0.2 | 15 | 24.0% 1.7 |
| 2-6 | 0.5 | 1.0 | 0.1 | 5 | 23.5% 4.1 |
| 2-7 | 0.5 | 1.0 | — | 30[3] | 30.1% 2.9 |
| 2-8 | 0.5 | 1.0 | 0.1 | 30[3] | 17.6% 0.7 |
| 2-9 | 0.5 | 0.1[1] | — | 15 | 20.4% 3.6 |
| 2-10 | 0.5 | 0.5[2] | — | 25 | 27.2% 2.1 |
| 2-11 | 0.5 | 5.0 | — | 25 | 36.2% 1.3 |
| 2-12 | 0.4 | 1.0 | — | 15 | 23.8% 1.2 |
| 2-13 | 0.3 | 1.0 | — | 15 | 24.9% 1.2 |
| 2-14 | 0.2 | 1.0 | — | 15 | 37.4% 2.0 |

[1] 0.9 g solvent added.
[2] 0.5 g solvent added.
[3] Room temperature.

EXAMPLE 3

A. Copolymer Preparation

Using the process and equipment of Part A of Example 1, four polymers were prepared using 2-isocyanatoethyl methacrylate (IEM), methyl methacrylate (MMA) and N,N'-dimethylacrylamide (DMAAM) as follows:

(a) 45/55 IEM/MMA 50 percent solids
(b) 25/75 IEM/DMAAM 50 percent solids
(c) 75/25 IEM/DMAAM 50 percent solids
(d) 100 IEM 26 percent solids

B. Immobilization

Following the process of Part B of Example 1, varying amounts of the polymers of Part A were combined with 1 g of Ampullariella species 3876 and 1 g of dibutyltin dilaurate catalyst (10 percent solution) and cured in a vacuum oven at room temperature for 30 minutes. The results are shown in Table III.

TABLE III

| Sample | Polymer Type | Polymer Amount (g) | Activity (% of Original) |
| --- | --- | --- | --- |
| 3-1 | a | 0.5 | 70.5 ± 3.84 |
| 3-2 | b | 1.1 | 73.0 ± 5.3 |
| 3-3 | b | 0.5 | 90.7 ± 5.7 |
| 3-4 | b | 1.2 | 74.7 ± 3.5 |
| 3-5 | c | 0.5 | 83.5 ± 4.5 |
| 3-6 | c | 1.0 | 78.9 ± 6.5 |
| 3-7 | d | 0.7 | 82.3 ± 4.9 |

These results show the surprisingly high activity of enzymes immobilized by the practice of this invention.

What is claimed is:

1. A process for chemically immobilizing biological material containing an active hydrogen moiety comprising:
   (a) contacting said biological material with a vinyl addition polymer comprising a biological immobilizing amount of a polymerized isocyanatoalkyl ester of an ethylenically unsaturated carboxylic acid whereby said vinyl addition polymer has pendent isocyanate groups, and
   (b) reacting said isocyanate groups pendent from the backbone of said vinyl addition polymer with said active hydrogen moieties of said biological material to immobilize said biological material.

2. The process of claim 1 wherein said vinyl addition polymer is a copolymer containing a monomer such that said copolymer is more hydrophilic than 40/60 weight percent copolymer of an isocyanate monomer and methyl methacrylate.

3. The process of claim 1 wherein said biological material is an enzyme.

4. The process of claim 1 wherein said biological material is a bacterial cell.

5. The bacterial cell of claim 4 which is Ampullariella species 3876, 3877, 3965 or 3966.

6. The Ampullariella species of claim 5 which is 3876.

7. The process of claim 1 wherein said isocyanatoalkyl ester is 2-isocyanatoethyl methacrylate.

8. The process of claim 1 wherein said vinyl addition polymer is a copolymer comprising 2-isocyanatoethyl methacrylate and N,N'-dimethylacrylamide.

9. A product formed from the process of claim 1.

10. The product of claim 9 wherein said vinyl addition polymer is a copolymer containing a monomer such that said copolymer is more hydrophilic than a 40/60 weight percent copolymer of an isocyanate monomer and methyl methacrylate.

11. The product of claim 9 wherein said biological material is an enzyme.

12. The product of claim 9 wherein said biological material is a bacterial cell.

13. The bacterial cell of claim 12 which is Ampullariella species 3876, 3877, 3965 or 3966.

14. The Ampullariella species of claim 13 which is 3876.

15. The product of claim 9 wherein said isocyanatoalkyl ester is 2-isocyanatoethyl methacrylate.

16. The product of claim 9 wherein said vinyl addition polymer is a copolymer comprising 2-isocyanatoethyl methacrylate and N,N'-dimethylacrylamide.

* * * * *